(12) United States Patent
Holmqvist

(10) Patent No.: US 8,876,783 B2
(45) Date of Patent: Nov. 4, 2014

(54) MEDICAMENT DELIVERY DEVICE

(75) Inventor: Anders Holmqvist, Värmdö (SE)

(73) Assignee: SHL Group AB, Nacka Strand (SE)

( * ) Notice: Subject to any disclaimer, the term of this patent is extended or adjusted under 35 U.S.C. 154(b) by 544 days.

(21) Appl. No.: 13/139,295

(22) PCT Filed: Nov. 26, 2009

(86) PCT No.: PCT/EP2009/065907
§ 371 (c)(1), (2), (4) Date: Aug. 12, 2011

(87) PCT Pub. No.: WO2010/066590
PCT Pub. Date: Jun. 17, 2010

(65) Prior Publication Data
US 2011/0288492 A1 Nov. 24, 2011

Related U.S. Application Data

(60) Provisional application No. 61/122,370, filed on Dec. 13, 2008.

(30) Foreign Application Priority Data

Dec. 12, 2008 (SE) .................................. 0850130-6

(51) Int. Cl.
| | |
|---|---|
| *A61M 5/00* | (2006.01) |
| *A61M 5/178* | (2006.01) |
| *A61M 5/315* | (2006.01) |
| *A61M 1/00* | (2006.01) |
| *A61M 5/20* | (2006.01) |

(52) U.S. Cl.
CPC ..... *A61M 5/2033* (2013.01); *A61M 2005/2086* (2013.01); *A61M 5/31511* (2013.01)

USPC ........... 604/208; 604/153; 604/187; 604/218; 604/230

(58) Field of Classification Search
CPC .............................................. A61M 2005/2086
USPC ........... 604/63, 135, 187, 208, 218, 232, 230, 604/131, 132, 133, 140, 150, 153
See application file for complete search history.

(56) References Cited

U.S. PATENT DOCUMENTS

| | | | | |
|---|---|---|---|---|
| 4,215,701 | A * | 8/1980 | Raitto | 600/576 |
| 5,549,573 | A * | 8/1996 | Waskonig | 604/218 |
| 6,565,531 | B1 * | 5/2003 | Mori et al. | 604/135 |
| 7,976,514 | B2 * | 7/2011 | Abry et al. | 604/246 |

FOREIGN PATENT DOCUMENTS

WO    WO 2007020090 A1 *    2/2007

* cited by examiner

*Primary Examiner* — Emily Schmidt
*Assistant Examiner* — Lauren M Peng
(74) *Attorney, Agent, or Firm* — Piedmont Intellectual Property

(57) ABSTRACT

The present invention relates to a medicament delivery device comprising a housing (12); a medicament container (14) arranged within said housing; medicament delivery drive means (22, 24); manually operable release means (38); and a movement speed control mechanism (44, 46, 48) comprising at least one fixed, flexible and elongated compartment (48) containing a liquid, and at least one flexible speed control member (44, 46) connected to the medicament delivery drive means; wherein said at least speed control member is arranged to be pressing on said at least one compartment for forcing said liquid past said member and thereby creating a movement speed control of said medicament delivery drive means when moved.

13 Claims, 3 Drawing Sheets

MEDICAMENT DELIVERY DEVICE

TECHNICAL AREA

The present invention relates to a medicament delivery device and in particular a device in which the duration of different operating steps may be controlled.

TECHNICAL BACKGROUND

There are many injectors on the market where the aim is to have high degrees of functionality and automatic features, such as in connection with mixing, penetration, injection, setting of dose, priming and covering of the needle after use. At the same time there is a demand on robustness, repeatability and reliability regarding the function, which sometimes might be difficult to meet when dealing with complex multi functions involving many interacting components. When there further are demands on low production costs, especially for devices that are to be used only once, the picture becomes even more complex.

There are in the patent literature numerous solutions to injection devices, the bulk of which never enter the market due to that they do not meet the demands in one way or the other. There is therefore a continuous search for solutions that provide the desired functions that at the same time fulfil the functional and/or economical demands.

Many devices having multi-functions that work in sequence, such as for example mixing, followed by priming, followed by penetration, followed by injection, followed by withdrawal, have a subsequent sequence triggered at the end of a previous sequence, for example when the needle has reached full penetration depth, the injection sequence is triggered. Many of these functions and sequences are initiated and performed by tensioned power springs that, when released, moves components of the delivery devices with a speed that is often determined by the force of the spring deducted by eventual counter forces such as friction, hydraulic resistance etc.

However, there is in many instances a desire that a sequence is performed in a controlled manner and possibly at rather slow speeds. One example is the mixing of medicament in a dual chamber cartridge. For some types of medicament, if the liquid is forced into the chamber containing powder medicament too fast, a foaming process is started, which foam later is difficult to remove, and thus negatively affects the preceding injection. Another example is injection of certain types of medicament which tend to cause pain when injected too fast due to that the tissue cannot absorb the medicament as fast as the medicament is injected. Yet an example is that there should be a delay from the end of injection until the medicament delivery device is removed from the injection site.

A few attempts have been made regarding controlling sequences of medicament delivery devices. One example is disclosed in WO 88/10129, where a slow delivery injection device is described. It comprises an injector having a spring acting on a plunger rod via a piston arranged in a stationary housing. Inside the spring a damper is arranged, having a valve for setting the damping resistance of the damper and thus the injection speed. The speed control according to WO 88/10129 is rather bulky and is not intended for, nor is it practical to implement in, a hand-held medicament delivery device such as for example a pen injector. Another example is disclosed in WO2007020090 A1.

There is thus a need for speed control mechanisms that are reliable, flexible, contain few components and are compact in order to be able to be utilized in hand-held medicament delivery devices.

BRIEF DESCRIPTION OF THE INVENTION

The aim of the present invention is to provide a medicament delivery device that remedies the drawbacks of the state of the art and that is able to provide a good speed control of sequences in a hand-held medicament delivery device.

This aim is obtained according to a main aspect with the features of the independent patent claim. Preferable embodiments of the present invention form the subject of the dependent patent claims.

According to a main aspect of the invention it is characterised by a medicament delivery device comprising a housing; medicament container arranged within said housing, wherein the container has a front opening with or for a medicament dispensing means for delivering the medicament therethrough and at least one movable stopper; medicament delivery drive means comprising an elongated plunger rod arranged in contact with the stopper, and a power source arranged to drive the plunger rod, and wherein said medicament delivery drive means are arranged to be movable from a cocked position to a released position within said medicament container and thereby capable of exerting a pressure on said stopper for expelling the medicament through the medicament dispensing means; operable release means arranged to be movable between a locked position in which said manually operable release means holds said medicament delivery drive means in its cocked position, and an activated position in which said manually operable release means releases the medicament delivery drive means; wherein the device comprises a movement speed control mechanism comprising at least one elongated and flexible compartment fixedly attached to the housing and wherein said compartment contains a volume of a viscous liquid, and at least one flexible speed control member extending from the plunger rod and having a contact surface arranged with longitudinally passages; wherein said contact surface is arranged to be pressed against said at least one compartment for forcing said liquid past said member and thereby creating a movement speed control of said medicament delivery drive means when said medicament delivery drive means is moved from its cocked position to its released position.

According to another aspect of the present invention, the at least one flexible speed control member 44 extends radially outward from the plunger rod and has an inclination towards the front end of the plunger rod, such that the higher the driving force, the higher pressure from the contact surface 46 against the flexible compartment.

According to a further aspect of the invention, the angle between the at least one flexible speed control member and the front end of the plunger rod is between 45° and less than 90°.

According to another aspect of the present invention, the power source is a compression spring arranged inside said plunger rod.

According to a further aspect of the invention, said contact surface has a shape of a circle segment.

According to yet a further aspect of the present invention, said compartment is arranged with varying volume, thereby creating different speeds along the compartment.

According to another aspect of the invention, the viscosity of the liquid may be altered in order to alter the speed control properties.

There are a number of advantages with the present invention. The use of a movement speed control mechanism provides the possibility to positively control the speed of different components and functions in a medicament delivery device. In this aspect the use of a "hydraulic" damper whereby liquid is squeezed through a narrow passage provides a reliable but yet simple solution with few parts.

The solution according to the invention further provides a number of possibilities for controlling and adjusting the speed of the different functions of the medicament delivery device. Thereby it is possible to adjust the speed depending on the desired and/or intended result. Thus the speed can be increased or decreased by altering the passage that the liquid is pressed through, by altering the viscosity of the liquid, by altering the volume of the liquid in the compartment or by altering the size of the passages on the contact surface. Moreover, the speed control of the medicament delivery is independent of the magnitude of the driving force from the power source, due to the configuration design of the at least one flexible speed control member.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
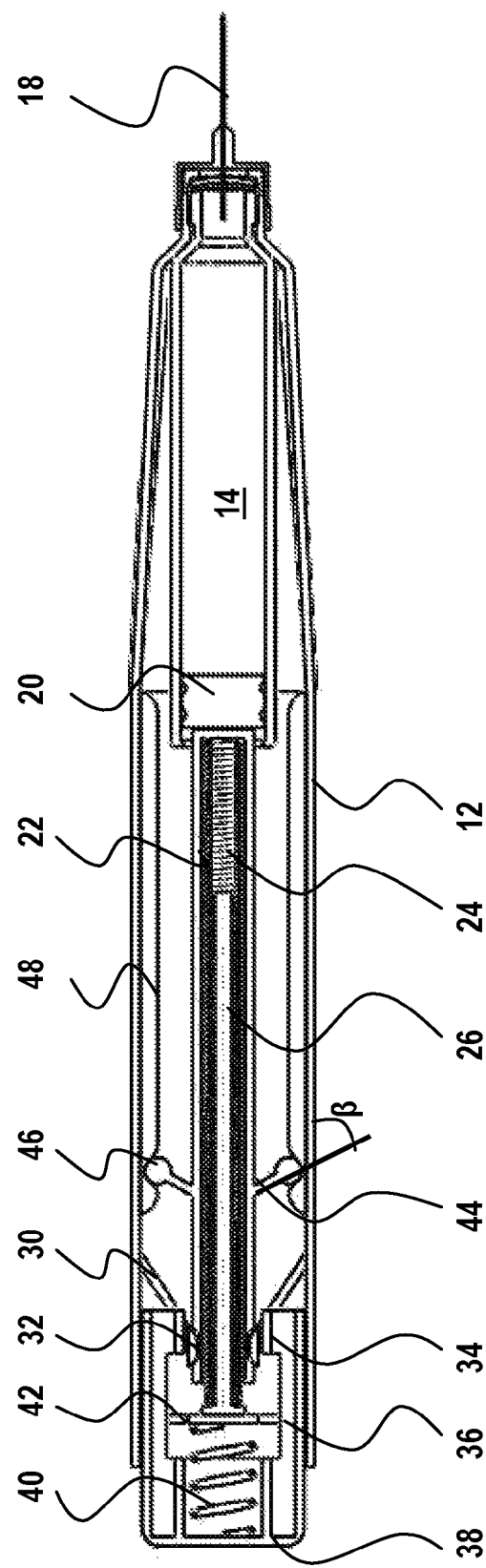
FIG. 1 is a side view in cross-section of an embodiment of the present invention.

FIG. 1 shows an example of a medicament delivery device according to the present invention, in the embodiment shown a medicament injector. It comprises a generally elongated housing 12. A medicament container 14 arranged within said housing, wherein the container has a front opening with or for a medicament dispensing means for delivering the medicament therethrough and at least one movable stopper 20. The housing in turn is arranged with a neck 16 onto which a medicament dispensing means 18 as e.g. an injection needle is attached.

The device comprises medicament delivery drive means arranged to be movable from a cocked position to a released position within said medicament container 14 and thereby capable of exerting a pressure on said stopper for expelling the medicament through the medicament dispensing means. The medicament delivery drive means comprises an elongated plunger rod 22 arranged at its front end in contact with the stopper, and a power source 24 arranged inside the plunger rod, in the embodiment shown as a compression spring. A guide rod 26 is further arranged inside the spring. When the medicament delivery drive means is in the cocked position, the spring 24 is tensioned accumulating a driving force and held in the tensioned position together with the plunger rod by a manually operable release means as it will be explained below. When the medicament delivery drive means is in the released position, the spring 24 is released within the container together with the plunger rod.

The manually operable release means is arranged to be movable between a locked position in which said manually operable release means holds said medicament delivery drive means in its cocked position, and an activated position in which said manually operable release means releases the medicament delivery drive means. The manually operable release means comprises an actuator 38 having arms 36 with ledges 34 at its free ends. Said ledges 34 are in contact with protrusions 32 of flexible arms 30 arranged on the inner surface of the housing when said manually operable release means is in the locked position.

Figure 2:
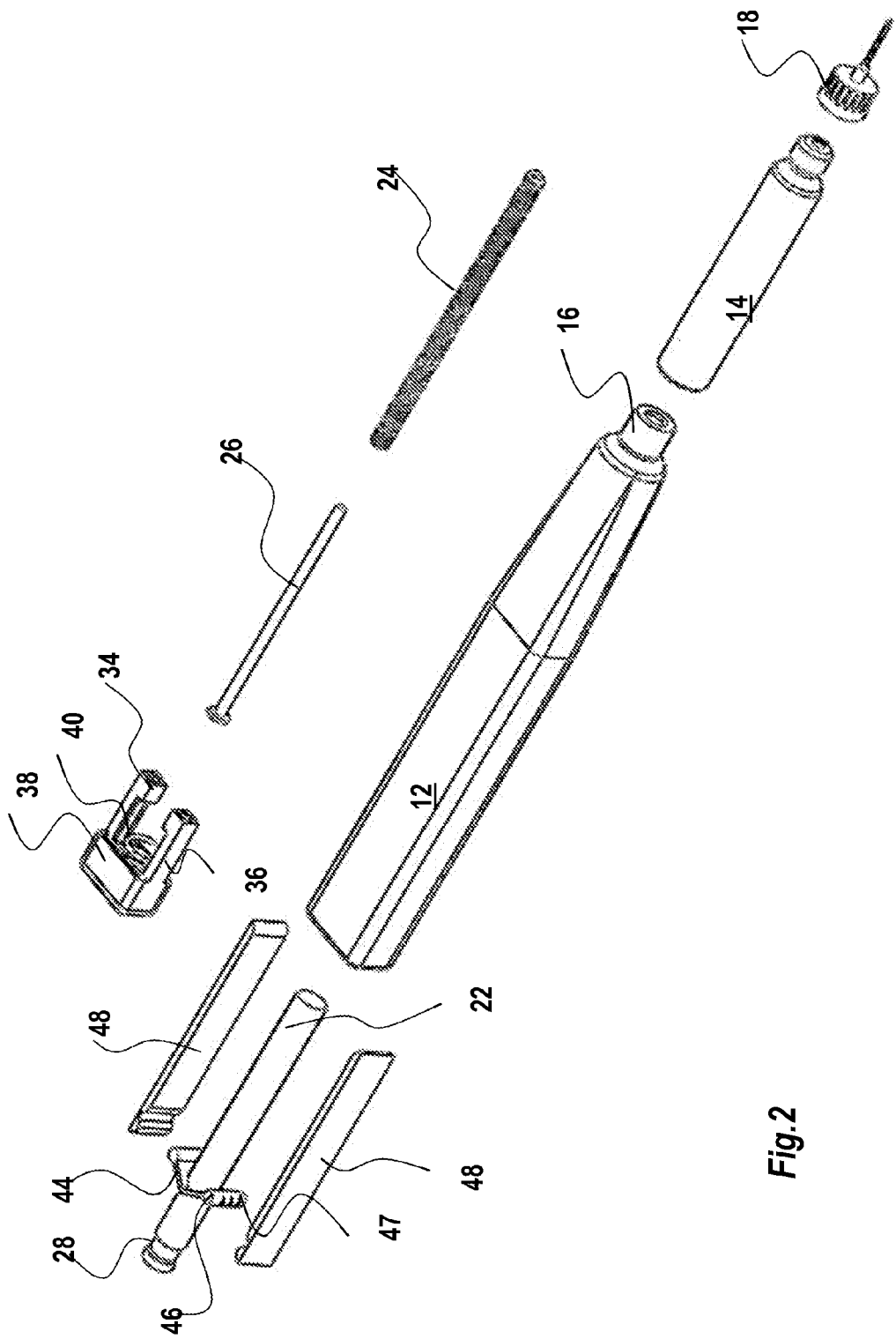
FIG. 2 is an exploded view of the embodiment of FIG. 1.

The rear end of the plunger rod, to the left in the figures, is arranged with a circumferential groove 28, FIG. 2. The protrusions 32 are initially positioned in the groove 28 e.g. a circumferential groove, when medicament delivery drive means is in the cocked position and the device is delivered to a user. The protrusions 32 are held in the circumferential groove by the inwardly projecting ledges 34 arranged on the arms 36 of the actuator 38, in the shown embodiment a push-button extending out of the rear end of the housing. A spring 40 is also arranged between an inner surface of the button and a fixed surface 42 of the housing.

According to the present invention the embodiment shown is arranged with a movement speed control mechanism comprising:—at least one elongated and flexible compartment 48, e.g. elongated flexible bags, fixedly attached to the housing and wherein said compartment contains a volume of a viscous liquid, and—at least one flexible speed control member 44 extending from the plunger rod and having a contact surface 46 arranged with longitudinally passages 47; wherein said contact surface is arranged to be pressed against said at least one compartment for forcing said liquid past said member and thereby creating a movement speed control of said medicament delivery drive means when said medicament delivery drive means is moved from its cocked position to its released position.

Said contact surface 46 has a shape of a circle segment as e.g. a roll, the reason and function of which will be described below. The volume of liquid in each bag as well as the force from each speed control member 44 is such that each contact surface 46 squeezes each bag at the contact point, as will be described below. The length of each flexible bag generally corresponds to the length of the delivery sequence in the embodiment shown. However, other lengths of the bags are feasible as will be described. Further, the at least one flexible speed control member 44 extends radially outward from the plunger rod and has an inclination towards the front end of the plunger rod, such that the higher the driving force, the higher pressure from the contact surface 46 against the flexible compartment. The angle between the at least one flexible speed control member 44 and the front end of the plunger rod is between 45° and less than 90°. With this configuration, the speed control of the medicament delivery is independent of the magnitude of the driving force.

The device is intended to function as follows. When the user is to take a dose of medicament, he/she attaches a medicament dispensing means 18 on the neck 16 of the device when necessary. The device is positioned on the delivery site and the user activates the manually operable release means from the locked position to the activated position by pressing the actuator 38. This causes the ledges 34 of the arms 36 to move out of contact with the protrusions 32, whereby these are free to move out of contact with the groove of the plunger rod 22. Due to the force of the compression spring, the plunger rod is moved forward, thereby moving the stopper 20 for expelling the medicament through the medicament dispensing means.

Figure 3:
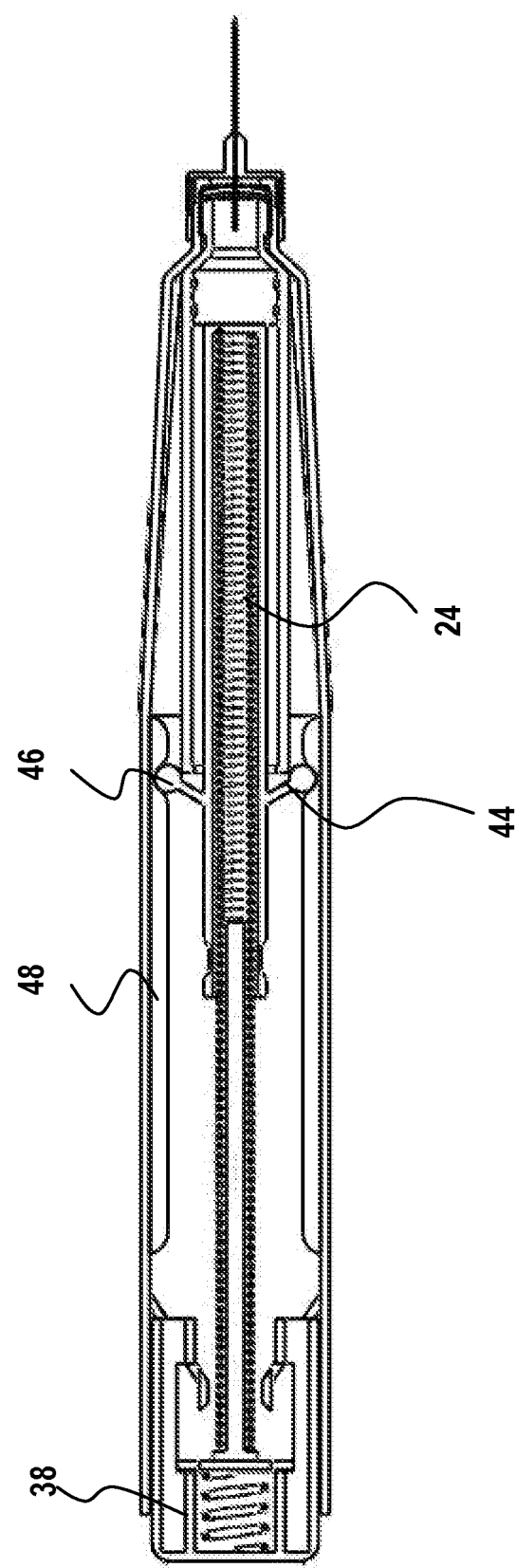
FIG. 3 is a side view in cross-section when the medicament has been delivered.

However, the movement of the plunger rod causes each contact surface 46 of each speed control member to be moved along each liquid bag 48, FIG. 3. Because of the pressing and squeezing action of each contact part 46, the liquid is forced through the longitudinally passages 47 of each contact surface, with the result that the movement of the plunger rod 22 is slowed down in an easy and reliable manner. Thus a speed controlled delivery movement is obtained with this type of hydraulic damper. Thus, the medicament delivery sequence is controlled in a very efficient and robust way.

From the above it is clear that the speed of the components arranged with the device according to the present invention may be modified in a number of ways depending on application and/or function. Thus the flexing properties of the speed control members 44 may be modified in order to increase/decrease the squeezing force. Further the contact surface 46 may have other shapes that affect the squeezing action and thereby the opening through which the liquid is squeezed. Also the liquid itself may be modified regarding its viscosity, thereby affecting the dampening or speed controlling properties. The liquid could for example be water or silicone oil. Further, the shape and size of the bags 48 may also be modified in order to change the properties of the damper. For example the bags may have different areas at the top and bottom of the bag, whereby the speed becomes variable during the movement. Moreover, the housing may be provided in its inner surface with longitudinal grooves that create openings for the liquid.

It is also possible to have the bags 48 arranged at only a part of the distance that a component is moving, like for example if one wishes to have the last part of the delivery sequence at a slower speed in order to ensure complete emptying of the medicament container, then the bags are arranged such that they are in contact with the contact parts during that part of the sequence. For the rest of the sequence the plunger rod moves with the speed that the spring provides. Due to the preferably flexible attachments 44 and the fact that they may be arranged with an angle β as seen in FIG. 1 a certain self-braking function is obtained.

It is further to be understood that the device according to the present invention may be used for other components and/or functions in a medicament delivery device. For example, the speed of a mixing action of a dual chamber cartridge may be controlled such that there is sufficient time to mix medicament with the liquid without the risk of foaming. Further, penetration movements and/or needle withdrawal movements may be controlled as well as be used as a delay function.

The wording medicament container may embrace several different types of containers such as cartridges, ampoules, syringes, vials, aerosol containers, just to mention a few. In that respect the present invention could also be used with other types of delivery devices such as powder or aerosol inhalers as well as nebulizers, with mouth pieces or nasal pieces and capable of delivering a dose of medicament to be inhaled by the patient.

It is further to be understood that other types of power sources can be used for the delivery of the medicament to a patient, such as clock springs, volute springs, pneumatic or hydraulic springs or any other type of non-electric power source suitable for the intended use according to the present invention.

It is to be understood that the embodiment described above and shown in the drawings is to be regarded only as a non-limiting example of the present invention and that it may be amended in many ways within the scope of the patent claims.

The invention claimed is:

1. A medicament delivery device, comprising:
a housing;
a medicament container arranged within the housing and having a front opening for a medicament dispenser for delivering a medicament therethrough and at least one movable stopper;
a medicament delivery driver, comprising an elongated plunger rod having a rear end and a front end, which is in contact with the stopper, and a power source arranged to drive the plunger rod, wherein the medicament delivery driver is movable from a cocked position to a released position within the medicament container, thereby exerting a pressure on the stopper for expelling the medicament through the medicament dispenser;
a manually operable release mechanism movable between a locked position, in which the manually operable release mechanism holds the medicament delivery driver in the cocked position, and an activated position, in which the manually operable release mechanism releases the medicament delivery driver; and
a movement speed control mechanism, comprising at least one elongated and flexible compartment fixedly attached to the housing and containing a volume of a viscous liquid, and at least one flexible speed control member extending from the plunger rod and having a contact surface arranged with longitudinal passages; wherein the contact surface is arranged to be pressed against the at least one compartment for forcing the viscous liquid past the at least one flexible speed control member and thereby controlling movement speed of the medicament delivery driver when the medicament delivery driver is moved from the cocked position to the released position;
wherein the at least one flexible speed control member extends radially outward from the plunger rod and has an inclination toward a front end of the plunger rod, such that a higher driving force produces a higher pressure from the contact surface against the flexible compartment.

2. The medicament delivery device of claim 1, wherein the power source is a compression spring arranged inside the plunger rod.

3. The medicament delivery device of claim 1, wherein the contact surface has a shape of a circle segment.

4. The medicament delivery device of claim 1, wherein the at least one compartment has a variable liquid volume, thereby creating different speeds.

5. The medicament delivery device of claim 1, wherein altering a viscosity of the viscous liquid alters the speed control.

6. The medicament delivery device of claim 1, wherein an angle between the at least one flexible speed control member and the front end of the plunger rod is greater than about 45° and less than about 90°.

7. The medicament delivery device of claim 1, wherein the power source is a compression spring arranged inside the plunger rod.

8. The medicament delivery device of claim 1, wherein the contact surface has a shape of a circle segment.

9. The medicament delivery device of claim 1, wherein the at least one compartment has a variable liquid volume, thereby creating different speeds.

10. The medicament delivery device of claim 1, wherein altering a viscosity of the viscous liquid alters the speed control.

11. The medicament delivery device of claim 1, wherein the manually operable release mechanism comprises an actuator having arms with ledges at free ends of the actuator, and the ledges contact protrusions of flexible arms arranged on the inner surface of the housing when the manually operable release mechanism is in the locked position.

12. The medicament delivery device of claim 11, wherein the protrusions contact a groove of the plunger rod when the medicament delivery driver is in the cocked position.

13. The medicament delivery device of claim 12, wherein the ledges are out of contact with the protrusions such that the protrusions are also out of contact with the groove when the manually operable release mechanism is in the activated position.

* * * * *